US012653439B2

(12) United States Patent (10) Patent No.: US 12,653,439 B2

Govari (45) Date of Patent: Jun. 16, 2026

(54) METHOD AND SYSTEM FOR IDENTIFICATION OF FRACTIONATED SIGNALS

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 294 days.

(21) Appl. No.: 18/219,740

(22) Filed: Jul. 10, 2023

(65) Prior Publication Data

US 2024/0032845 A1 Feb. 1, 2024

Related U.S. Application Data

(60) Provisional application No. 63/392,521, filed on Jul. 27, 2022.

(51) Int. Cl.
*A61B 5/361* (2021.01)
*A61B 5/00* (2006.01)
(Continued)

(52) U.S. Cl.
CPC ............... *A61B 5/361* (2021.01); *A61B 5/287* (2021.01); *A61B 5/339* (2021.01); *A61B 5/367* (2021.01); *A61B 5/7246* (2013.01); *A61B 5/7289* (2013.01)

(58) Field of Classification Search
CPC ......... A61B 5/361; A61B 5/339; A61B 5/367; A61B 5/287; A61B 5/7246; A61B 5/7289; A61B 2018/00267; A61B 2018/00351; A61B 2018/00613; A61B 2018/00636; A61B 2018/00666; A61B 2018/00678; A61B 2018/00839

(Continued)

(56) References Cited

U.S. PATENT DOCUMENTS 8,676,305 B2 3/2014 Hayam et al.
9,629,567 B2 4/2017 Porath et al.
(Continued)

FOREIGN PATENT DOCUMENTS

CA 3121576 A1 6/2020

OTHER PUBLICATIONS

European Search Report for corresponding EPA No. 23187732.5 dated U.S. Appl. No. 11/032,023.

*Primary Examiner* — Beverly M Flanagan

(57) ABSTRACT

A method, apparatus and computer program product, the method comprising obtaining a first electrical signal from a catheter comprising a first electrode distally disposed thereon, when the catheter is inserted into a heart chamber of a heart and the first electrode does not touch a chamber wall; performing statistical analysis of the first electrical signal to obtain a first characteristic of the first electrical signal; obtaining a second electrical signal from the catheter, when a second electrode touches a point on the chamber wall; performing statistical analysis of the second electrical signal to obtain a second characteristic of the second electrical signal; determining a similarity measure between the first characteristic and the second characteristic; and subject to the similarity being below a predetermined threshold, indicating the region as potentially belonging to an arrhythmogenic region of the heart.

17 Claims, 6 Drawing Sheets

(51) Int. Cl.
*A61B 5/287* (2021.01)
*A61B 5/339* (2021.01)
*A61B 5/367* (2021.01)

(58) Field of Classification Search
USPC .......................................................... 606/41
See application file for complete search history.

(56) References Cited

U.S. PATENT DOCUMENTS

| | | | | |
|---|---|---|---|---|
| 2006/0111703 | A1* | 5/2006 | Kunis | ................. A61B 18/1492 606/41 |
| 2015/0080752 | A1* | 3/2015 | Lian | ........................ A61B 5/341 600/512 |
| 2017/0065198 | A1* | 3/2017 | Ruppersberg | .......... A61B 5/341 |
| 2019/0216346 | A1* | 7/2019 | Ghodrati | .............. A61B 5/7203 |
| 2020/0297281 | A1* | 9/2020 | Basu | .................... A61B 5/6859 |
| 2021/0068694 | A1 | 3/2021 | Chou | |
| 2021/0378579 | A1 | 12/2021 | Doron | |
| 2022/0400951 | A1 | 12/2022 | Haeusser et al. | |
| 2022/0400952 | A1* | 12/2022 | Srivastava | ............. G16H 40/63 |

* cited by examiner

METHOD AND SYSTEM FOR IDENTIFICATION OF FRACTIONATED SIGNALS

CROSS-REFERENCE TO RELATED APPLICATION

This application claims the benefit of provisional patent application No. 63/392,521, titled "Method and System for Identification of Fractionated Signals" filed Jul. 27, 2022, which is hereby incorporated by reference in its entirety without giving rise to disavowment.

FIELD OF THE DISCLOSURE

This disclosure relates generally to analysis of electro-physiological (EP) signals, and specifically to a method for identifying fractionated signals originated at a location in the heart.

BACKGROUND OF THE DISCLOSURE

Arrhythmias may be caused by problems with the electrical conduction system of the heart, and in particular electrical activity in one or more points or areas on a wall of a heart chamber. Atrial fibrillation is an arrhythmia characterized by disorganized signals that make the atria (left and/or right atria) squeeze very fast and in an asynchronous cardiac rhythm.

A common treatment of atrial fibrillation, also referred to as A-fib, is ablation which uses energy to create scars on one or more active areas on the heart wall, in order to block faulty electrical signals that contribute to the disorganized signals, and to restore typical heartbeat.

BRIEF DESCRIPTION OF THE DRAWINGS

The present disclosure will be more fully understood from the following detailed description of the examples thereof, taken together with the drawings, in which.

DETAILED DESCRIPTION OF EXAMPLES

Figure 1:
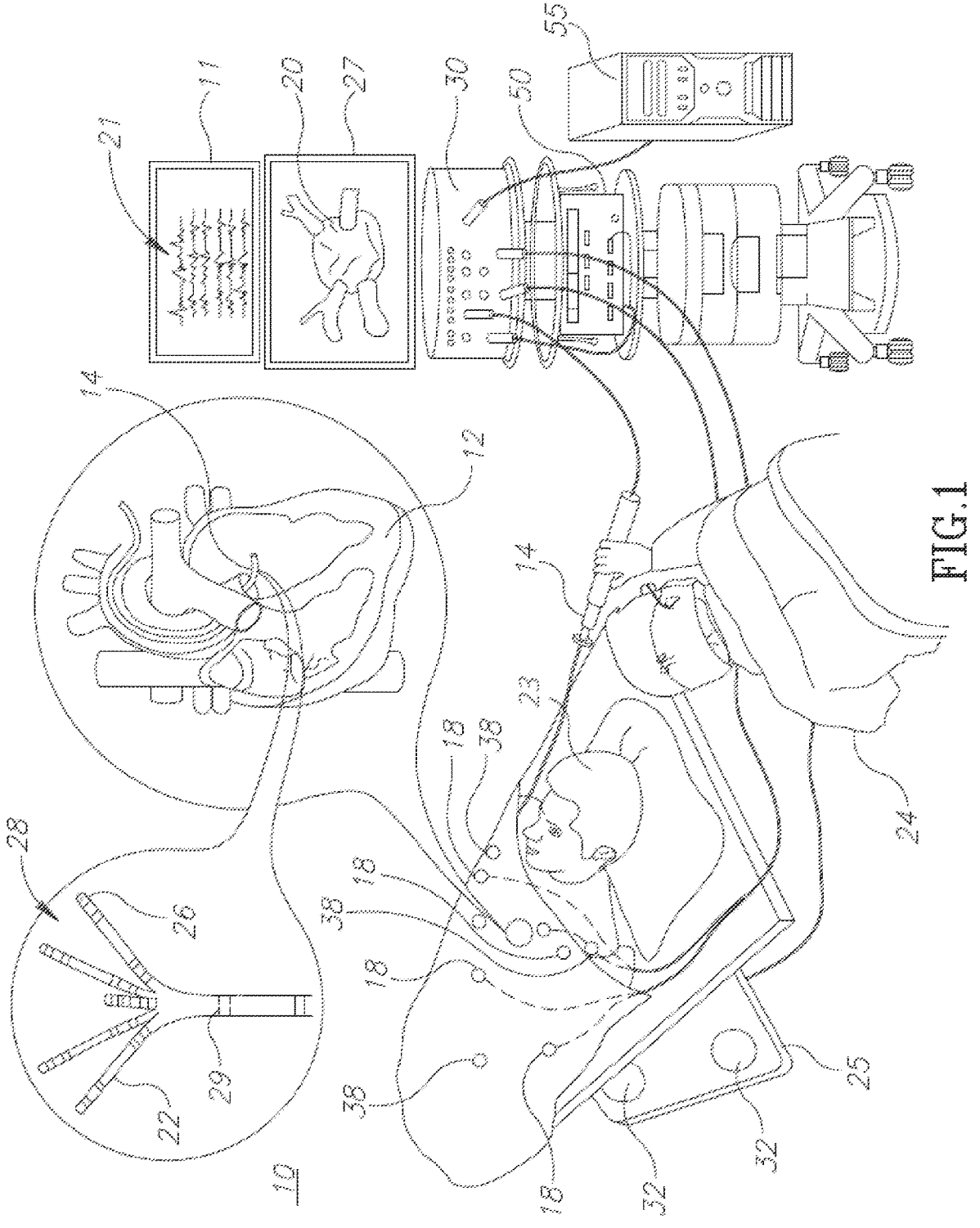
FIG. 1 is a schematic, pictorial illustration of a catheter-based electrophysiological (EP) mapping and ablation system, in accordance with some exemplary embodiments of the disclosure.

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

Software programming code, which embodies aspects of the present invention, is typically maintained in permanent storage, such as a computer readable medium. In a client-server environment, such software programming code may be stored on a client or a server. The software programming code may be embodied on any of a variety of known media for use with a data processing system. This includes, but is not limited to, magnetic and optical storage devices such as disk drives, magnetic tape, compact discs (CD's), digital video discs (DVD's), and computer instruction signals embodied in a transmission medium with or without a carrier wave upon which the signals are modulated. For example, the transmission medium may include a communications network, such as the Internet. In addition, while the invention may be embodied in computer software, the functions necessary to implement the invention may alternatively be embodied in part or in whole using hardware components such as application-specific integrated circuits or other hardware, or some combination of hardware components and software.

Overview

Arrhythmogenic tissue related to atrial fibrillation may be identified by inspecting Intracardiac Electrogram (IEGM) at one or more locations along an atria wall, e.g., inner wall, to detect the local potential caused by depolarization in each of the one or more locations. Locations at which the IEGM produced a fractionated signals may indicate locations including arrhythmogenic tissue related to the atrial fibrillation.

The IEGM is typically detected with one or more electrodes, and/or one or more pairs of electrodes, on a distal tip of an intracardiac catheter. In some example embodiments, the intracardiac catheter additionally includes a position sensor configured to track position of the distal tip. Optionally, intracardiac catheter may also include contact or force sensing capability, e.g., a force sensor configured to sense whether there is contact between the distal tip and the atrial wall or the force applied by the distal tip on the atrial wall.

The presence of noise within the signal poses a significant challenge when attempting to identify arrhythmogenic tissue from an IEGM. The noise is typically due to electrical devices operating in the ambient environment, as well as due to depolarization of the surrounding tissue (far-field signals). It is often difficult to isolate the local potential from the noise, e.g., ambient noise or far field signal, and therefore difficult to correctly distinguish between a noisy signal captured from healthy tissue and a fractionated signal captured from arrhythmogenic tissue.

Typically, the signals captured are bi-polar signals detected as potential differences between two closely spaced electrodes on the catheter.

According to some example embodiments, a statistical approach is provided to improve detection of fractionated signals and to reduce false positive detections. Optionally, locations at which a fractionated signal is detected may be reported to a physician for further analysis to determine their clinical significance.

According to some example embodiments, the statistical method includes performing autocorrelation on signals captured from electrodes immersed in a blood pool in the vicinity of the area of interest, for the purpose of characterizing a signal that only includes the noise, e.g., ambient noise and far-field signal. Since the electrodes are immersed in the blood pool as opposed to touching the chamber wall, the local potential is not expected to appear in the captured signal.

According to some example embodiments, the statistical method additionally includes performing autocorrelation on signals captured with electrodes touching the area of interest on the chamber wall, e.g., an area producing an IEGM with fractionated looking morphology. The autocorrelation of the signals captured in the area of interest provide for characterizing the potentially fractionated signal, e.g., the local potential, as well as the noise (ambient noise and far field signal).

According to some example embodiments, the characterizing features obtained from autocorrelation of the signals captured in the blood pool are compared to the characterizing features obtained from autocorrelation of the signals captured on the chamber wall. Optionally, autocorrelation coefficients are compared.

It is appreciated that the statistical analysis may be performed on an aggregation of multiple signals provided by multiple electrodes. The aggregation of the signals may be an average signal, average with removed outliers, or the like, as detailed below.

If the comparison results are that the two series of autocorrelation coefficients are similar, for example the distance therebetween according to some predetermined metrics is lower than a predetermined threshold, then it may be assumed that a fractionated looking morphology of the IEGM captured from the chamber wall is mainly due to the noise.

If, however, the two sets of autocorrelation coefficients are substantially different, than it may be assumed that the fractionated looking morphology of the IEGM captured from the chamber wall may be due to potentially arrhythmogenic tissue. In such a case, the IEGM detected on the chamber wall may be identified as a fractionated signal, and may then be further investigated.

Further signals may then be sensed at other locations on the wall of the same chamber by different electrodes touching the chamber wall. The autocorrelation results for the further signals may also be compared to the already available autocorrelation coefficients of the initially obtained noise signal. When moving further to investigate other chambers of the heart, a new noise signal taken with the electrodes not touching the wall of the newly visited chamber may be obtained and processed, and compared to one or more other signals taken when one or more electrodes do touch the wall.

The method may thus provide for determining in a robust manner whether a certain area of the heart generates fractionated signal. The fractionated areas may optionally be annotated on an anatomical map of the heart. The annotation may then be useful in determining whether and which areas of the heart should be ablated.

System Description

Reference is made to FIG. 1 showing an example catheter-based electrophysiology mapping and ablation system 10. System 10 includes one or more catheters, which are percutaneously inserted by physician 24 through the patient's vascular system into a chamber or vascular structure of heart 12. The plurality of catheters may include catheters dedicated for sensing Intracardiac Electrogram (IEGM) signals, catheters dedicated for ablating and/or catheters for both sensing and ablating. An example catheter 14 that is configured for sensing IEGM is illustrated herein. Physician 24 brings a distal tip 28 of catheter 14 into contact with the heart wall for sensing a target site in heart 12. For ablation, physician 24 would similarly bring a distal end of an ablation catheter to a target site for ablating.

Catheter 14 is an exemplary catheter that includes one and preferably multiple electrodes 26 optionally distributed over a plurality of splines 22 at distal tip 28 and configured to sense the IEGM signals. Catheter 14 may additionally include a position sensor 29 mounted on or near distal tip 28 for tracking position and orientation of distal tip 28. Optionally and preferably, position sensor 29 is a magnetic based position sensor including three magnetic coils for sensing three-dimensional (3D) position and orientation.

Magnetic based position sensor 29 may be operated together with a location pad 25 including a plurality of magnetic coils 32 configured to generate magnetic fields in a predefined working volume. Real time position of catheter 14 may be tracked based on magnetic fields generated with location pad 25 and sensed by magnetic based position sensor 29.

Optionally, system 10 includes one or more electrode patches 38 positioned on patient 23 to establish location reference for location pad 25 as well as impedance-based tracking of electrodes 26. For impedance-based tracking, electrical current is directed toward electrodes 26 and sensed at patches 38.

A recorder 11 displays electrograms 21 captured by body surface ECG electrodes 18 and intracardiac electrograms (IEGM) captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more of electrodes at a distal tip of a catheter configured for ablating.

Patient interface unit (PIU) 30 is an interface configured to establish electrical communication for catheters, electrophysiological equipment, and a workstation 55 is configured for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 includes memory, processing and user interface capability. Workstation 55 may provide multiple functions, optionally including (1) modeling the endocardial anatomy in three dimensions (3D) and rendering the model or anatomical map 20 for display on a first display device 27; (2) displaying on display device 27 activation sequences (or other data) compiled from recorded electrograms 21 in representative visual indicia or imagery superimposed on the rendered anatomical map 20; (3) displaying real-time location and orientation of multiple catheters within the heart chamber; and (5) displaying on display 27 sites of interest such as places where ablation energy has been applied. One commercial product embodying elements of the system 10 is available as the CARTO 3 System, available from Biosense Webster, Inc., 3333 Diamond Canyon Road, Diamond Bar, Calif. 91765.

Figure 2A:
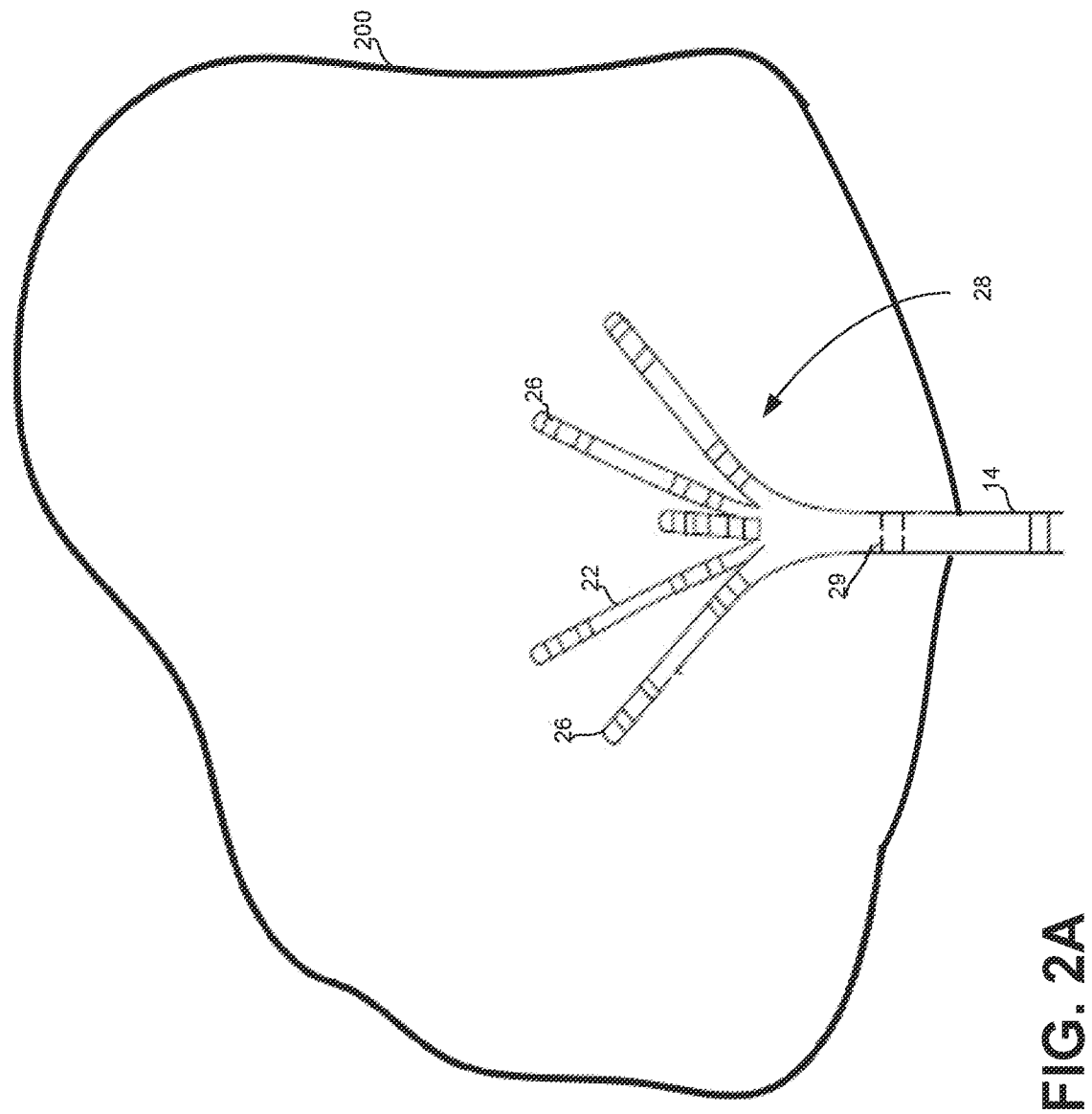
FIG. 2A and FIG. 2B show two exemplary positions of a mapping catheter within an atrium of a subject, in accordance with some exemplary embodiments of the disclosure.
Figure 2B:
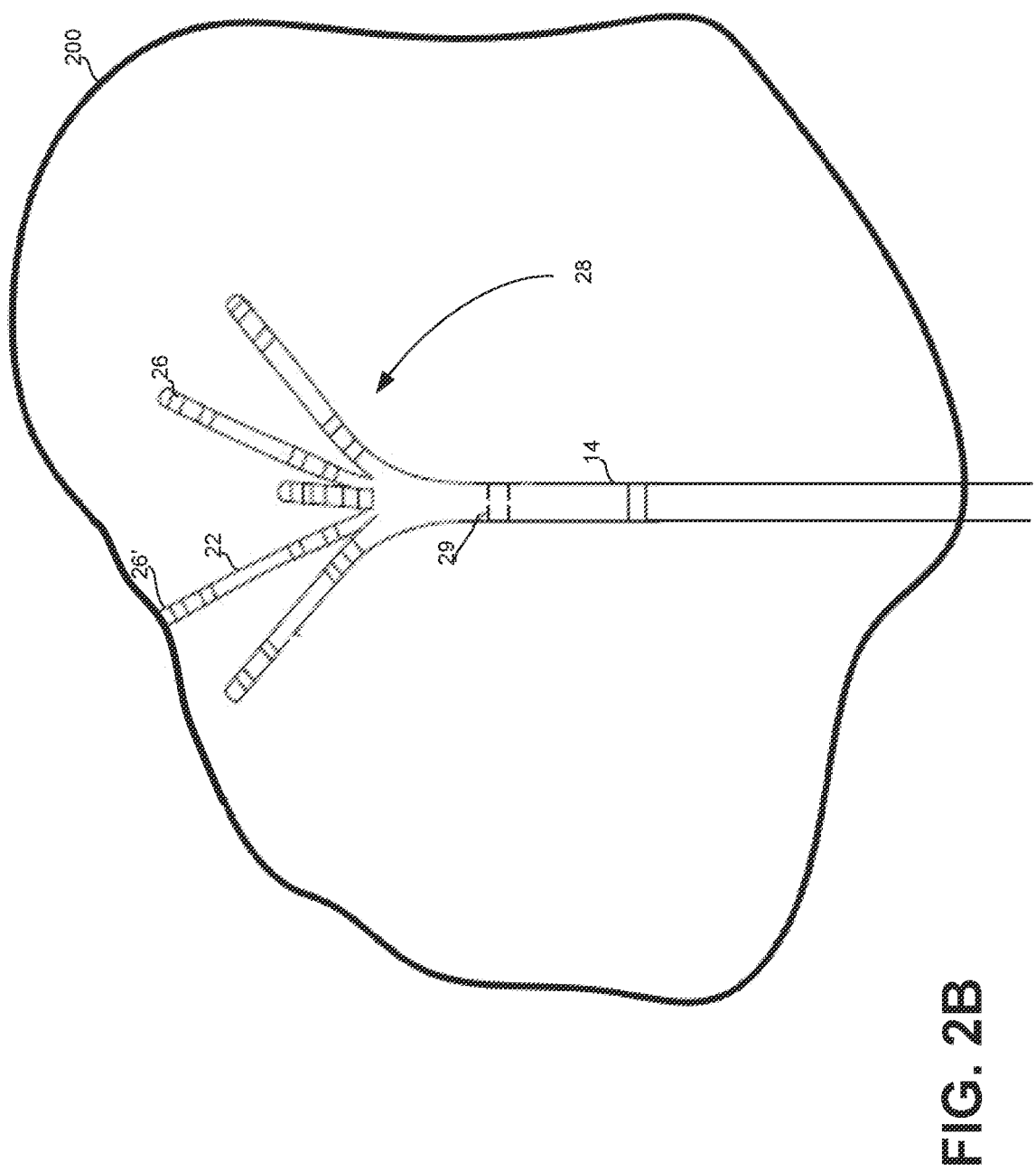

Referring now to FIG. 2A and FIG. 2B, showing two exemplary positions of a catheter with multiple electrodes 26 located on spline 22 of catheter 14 within a heart chamber

200 of a patient, in accordance with some exemplary embodiments of the disclosure.

FIG. 2A shows electrodes 26 located at distal tip 28 of catheter 14, wherein electrodes 26 are displaced from the tissue, for example positioned in the internal volume of heart chamber 200, e.g., immersed in the blood pool without touching the wall of the chamber. Additionally or alternatively, electrodes 26 may be positioned inside a vein or an artery, where there is no electrical activation. The electrodes thus sense ambient noise and far-field signals or the like, which are generally referred to as noise.

FIG. 2B shows electrodes 26 wherein one or more electrode 26' touch the wall of heart chamber 200, e.g., the atrium, and thus sense the electrical signal originating from the tissue, in addition to the noise as sensed by electrodes 26 in FIG. 2A. If the sensed signal is not fractionated, the fractionated looking morphology of the sensed signal is expected to have statistical characteristics similar to those of the signal as sensed by electrodes 26 in FIG. 2A, and comprised substantially of the noise.

The term "correlation" as used herein refers to a measure of similarity between two series or functions, wherein the measure is a function of the displacement of one series or function relative to the other.

Autocorrelation refers to the same measure of similarity, but between a series or function (collectively referred to as function) and itself, at various displacements. In other words, autocorrelation measures the correlation, if any, between observations at different temporal distances apart, and thus provides useful descriptive information of the function, such as a signal. The function may thus be characterized as a series of autocorrelation coefficients $r_k$, each indicating the similarity of the function to itself at a temporal displacement of k, wherein k may be an index for a series, a real number for a function, or the like.

An autocorrelation coefficient of a function x at displacement k may be approximated by the following formula:

$$r_k = \frac{\sum_{t=1}^{N-k}(x_t - \bar{x})(x_{t+k} - \bar{x})}{\sum_{t=1}^{N-k}(x_t - \bar{x})_2}$$

Wherein:

N is the number of observations to be tested, and may be set according to the required resolution;

$\bar{x}$ is an average value of the function, an autoregressive moving average (ARMA) over a section of the function, or an autoregressive integrated moving average (ARIMA); and $\bar{x}$ is subtracted from $x_t$ and from $x_{t+k}$ in order to obtain a normalized value, in the range of $[-1 \ldots 1]$.

Figures 3A, 3B:
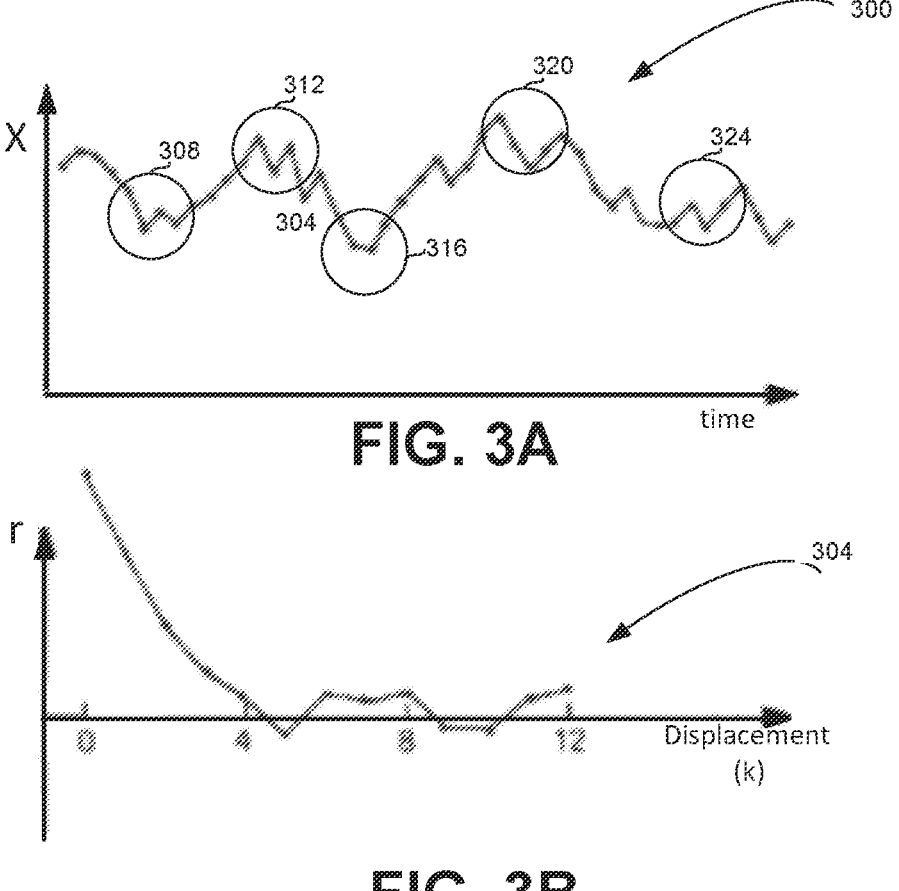
FIG. 3A shows a graph of function 300 x(t)
FIG. 3B shows the corresponding graph of the autocorrelation coefficients $R_K$ of x(t), in accordance with some exemplary embodiments of the disclosure.

FIG. 3A shows a graph of function 300 x(t), and FIG. 3B shows the corresponding graph of the autocorrelation coefficients $r_k$ of x(t).

It is appreciated that for any function, $r_0$ will always be 1, as shown in graph 304, since a function is identical to itself if no displacement is introduced.

It is seen that multiple areas of x(t) comprise a sequence of values that are close in time (for example 1 or 2 time-units apart) and have similar values, as shown in areas 308, 312, 316, 320 and 324. This explains the relatively high values of $r_1$ and $r_2$, representing the similarity of the signal to itself at these small displacements.

Figure 4:
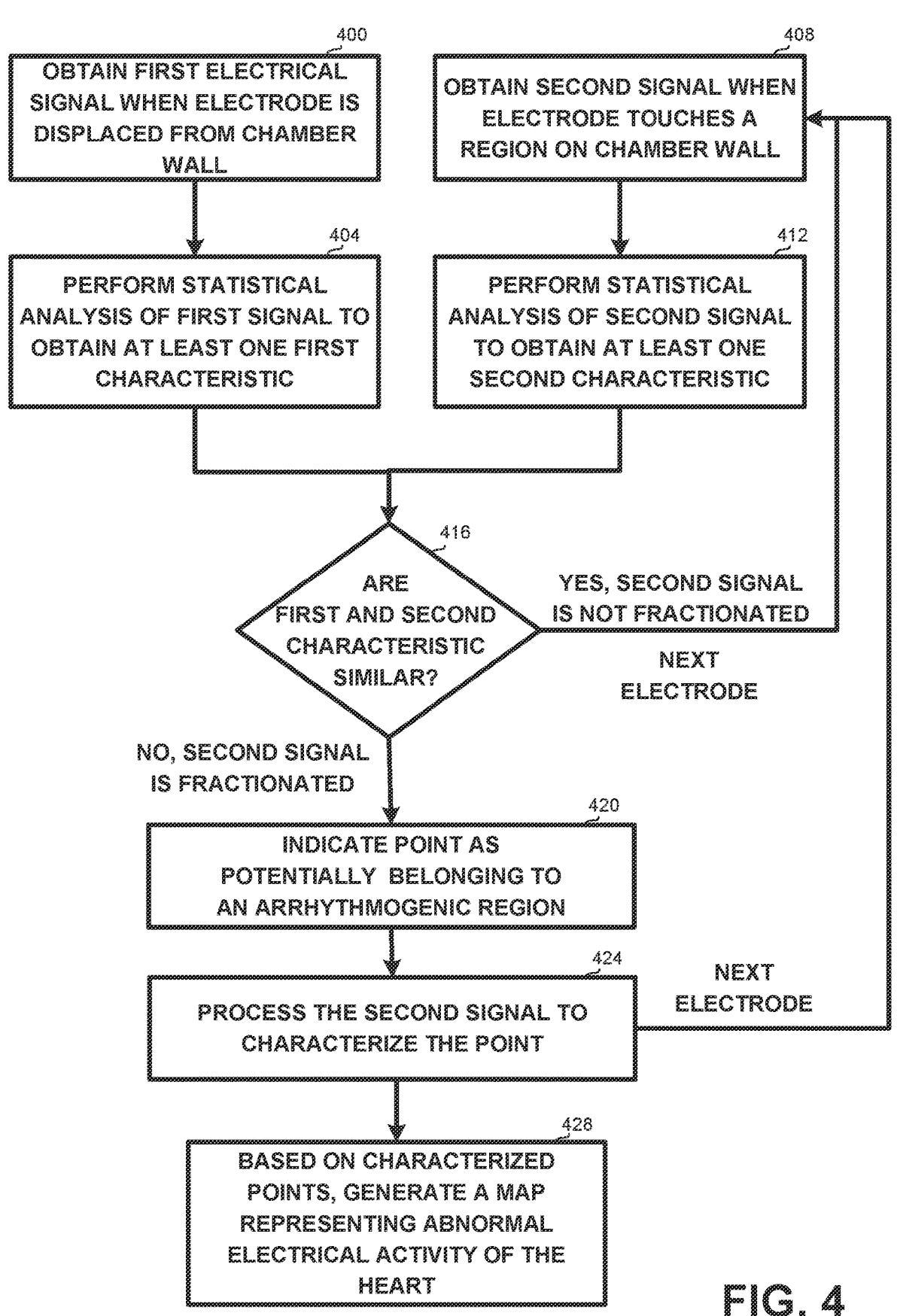
FIG. 4 is a flowchart of steps in a method for determining whether a region in the heart generates a fractionated signal, in accordance with some exemplary embodiments of the disclosure.

Referring now to FIG. 4, showing a flowchart of steps in a method for determining whether a region in the heart generates a fractionated signal, in accordance with some exemplary embodiments of the disclosure.

On step 400, a first electrical signal, e.g., an IEGM signal may be obtained during a catheterization operation when an electrode connected at the distal tip of the probe is positioned within the blood pool and is displaced from the chamber wall.

Since multiple electrodes which are positioned on one or more splines may be used to provide multiple signals, the first electrical signal may be any aggregation of the multiple signals. The aggregation method may be an average of the signals, the average after outliers have been removed, or any other aggregation method.

In some embodiments, in order not to include in the aggregation those signals provided by electrodes that touch the chamber wall, a touch sensor may be used for determining whether each electrode touches the chamber wall. Such mechanism may comprise a force sensor, impedance detection with electrodes 26 or any other suitable sensor. The signals provided by electrodes that touch the chamber wall may not be aggregated with the other signals for characterizing the noise, e.g., may be excluded when generating the first electrical signal.

On step 404, statistical analysis may be performed over the signal obtained on step 400. The statistical analysis may obtain one or more characteristics of the signal, for example the autocorrelation coefficients $r_k$ of the signal as exemplified in association with FIG. 3A and FIG. 3B above. For example, a series of coefficients, for example up to 10 coefficients, may be calculated over a time window of tens of seconds, for example 0 to about 20 seconds, 0 to about 60 seconds, or the like. It is appreciated that the plurality of electrodes enables the simultaneous collection of significant amount of data over a short period of time. Thus, the more electrodes are being used, the shorter is the time required for collecting the data.

On step 408, one or more second electrical signals may be obtained during the catheterization, when one or more of the electrodes is positioned such that it is in contact the chamber wall. Determining whether an electrode is in contact with the heart wall may be performed by a sensor such as a force sensor, as detailed above.

On step 412, the same statistical analysis as performed on step 404 may be performed over the one or more signals obtained on step 408. The one or more signals may be captured by a plurality of electrodes in proximity to one another and covering a selected area. The statistical analysis may obtain one or more characteristics of each signal, for example the autocorrelation coefficients $r_k$ as detailed in association with FIG. 3A and FIG. 3B above. For example, a series of coefficients may be calculated over a time window as detailed above.

On step 416, the characteristics obtained on steps 404 and 412 for the first and second signals, respectively, may be compared.

Comparison may be in accordance with any required metric. In one example, the metric may be the number of corresponding $r_k$ pairs that are within a predetermined difference, or within predetermined ratios from one another. For example, if the first coefficients of the first signal, as calculated on step 404 are $r_{1,0}=0.75$, $r_{1,1}=0.5$, $r_{1,2}=0.8$, $r_{1,3}=-0.4$, the second coefficients of the second signal, as calculated on step 412 are $r_{2,0}=0.7$, $r_{2,1}=0.1$, $r_{2,2}=-0.1$, $r_{2,3}=-0.3$, and the predetermined difference is 0.2, then the first and the last coefficient pairs ($r_{1,0}=0.75$, $r_{2,0}=0.7$) and ($r_{1,3}=-0.4$, $r_{2,3}=-0.3$) are within the predetermined difference. If the number of such pairs, two in this example, is equal to or exceeds a second threshold, the characteristics and hence the associated signals may be determined to be similar. Thus, if the second predetermined threshold is 1 or 2, then the characteristics are considered to be similar, and if the second predetermined threshold is higher than 2, then the characteristics are not considered to be similar.

It is appreciated that the metric described above is exemplary only, and any other relevant metric may be used, for a non-limiting example a square root of the sum of squared differences.

If the statistical signature, for example the series of $r_k$ coefficients, of the signal captured on the chamber wall does not significantly deviate from the statistical signature measured in the blood pool, the area from which the signals are obtained may be marked as an area with healthy tissue, e.g., an area that does not produce fractionated signals. Execution may then return to step 408, where the process may be repeated for another electrode or group of electrodes touching the chamber wall.

If the statistical signature of the signal captured on the chamber wall significantly deviates from the statistical signature measured in the blood pool, this may be an indication that the area on the chamber wall from which the signal has been obtained is an arrhythmogenic region of the heart which emits a fractionated signal.

On step 420 the location of the electrode may be indicated, for example stored in a storage device as potentially belonging to an arrhythmogenic region of the heart, e.g., a scarred region and/or a fibrotic region.

On step 424 the signal obtained on step 408 may be further processed, in order to characterize the arrythmia at the region, for example the signal intensity may be obtained.

Execution may then return to step 408 for obtaining signals produced by further electrodes or electrode groups that touch the chamber wall.

Once the signals provided by the electrodes that touch the chamber wall have been processed, the probe may be moved to another location where one or more electrodes are touching further areas on the chamber wall and repeating the process.

It is appreciated that all the signals taken by electrodes touching the chamber wall may be statistically compared to the signals taken at the blood pool of the chamber.

It is appreciated that the steps above may be repeated for one or more additional chambers of the heart.

It is also appreciated that in situations where one or more electrodes touch the heart wall, and other one or more electrodes do not touch the heart wall, steps 400 and 404 may be performed substantially in parallel to steps 408 and 412, and without the physician moving the catheter.

On step 428, a map representing the electrical activity of the heart may be generated, for example a visual representation showing in brighter colors areas that are more arrhythmogenic, in lighter colors areas that are less arrhythmogenic, and with no color areas that are not arrhythmogenic. It is appreciated that any other visualization may be used, such as using patterns, shades, graphics, or the like.

Optionally, the physician may select regions to ablate based on the map presented.

It is appreciated that ablating a region may be performed after discovering that the region is arrhythmogenic, after mapping the whole heart or parts thereof, or the like.

Figure 5:
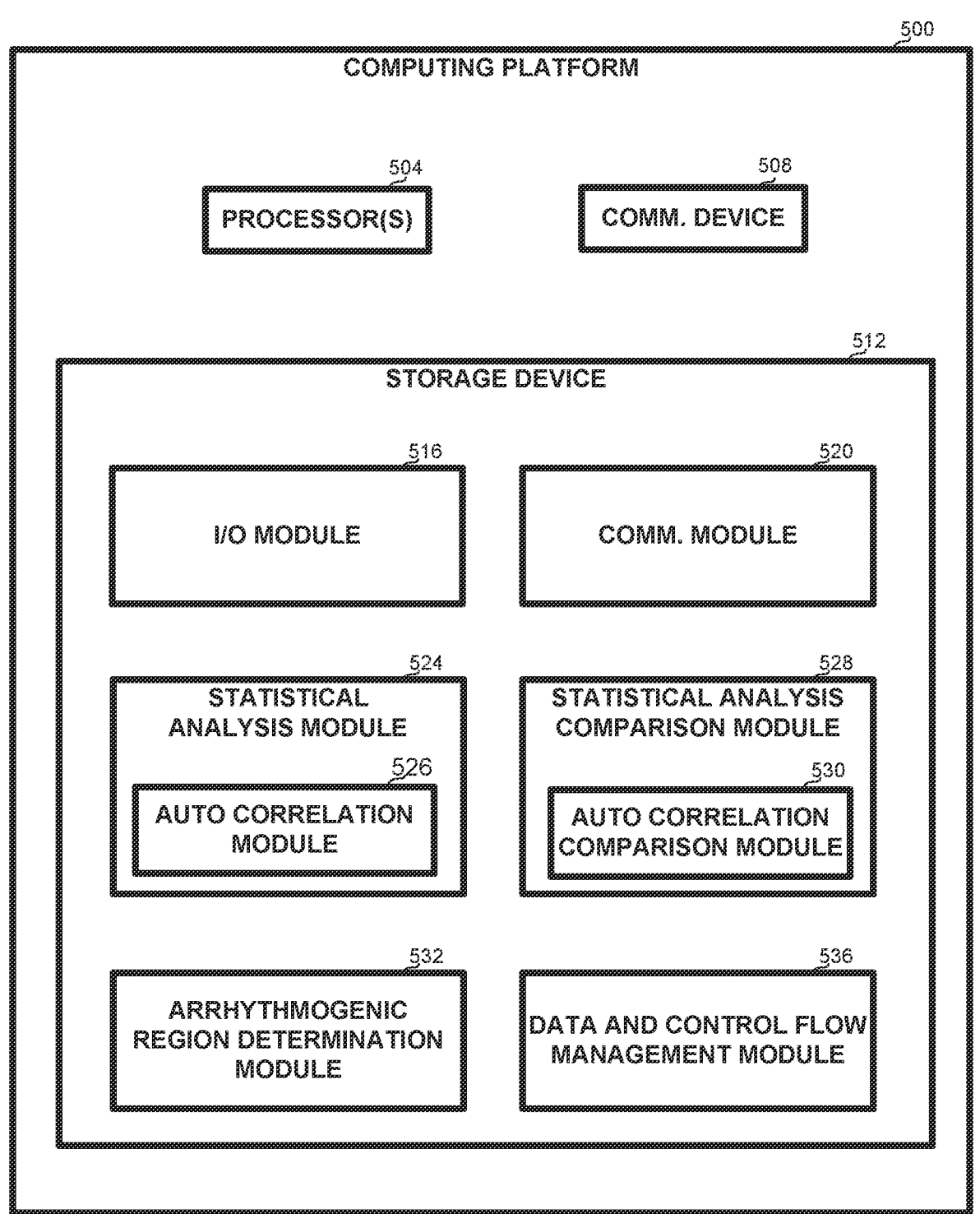
FIG. 5 is a schematic block diagram of a computing platform for determining whether a region in the heart generates a fractionated signal and annotating a map of the heart, in accordance with some exemplary embodiments of the disclosure.

Referring now to FIG. 5, showing a block diagram of a computing platform 500 for determining whether a region in the heart generates a fractionated signal and annotating a map of the heart, in accordance with some exemplary embodiments of the disclosure.

It will be appreciated that computing platform 500 may be embedded within console 30, but may also be a standalone computing platform or embedded elsewhere and be in operative communication with console 30.

Computing platform 500 may be implemented as one or more computing platforms which may be operatively connected to each other, for example, one or more remote computing platforms, which may be implemented for example on a cloud computer. Other computing platforms may be a part of a computer network of the associated organization. In other embodiments, all the functionality may be provided by one or more computing platforms all being a part of the organization network.

Computing platform 500 may comprise one or more processors 504 located on the same computing platform or not, which may be one or more Central Processing Units (CPUs), microprocessors, electronic circuits, Integrated Circuits (IC) or the like. Processor 504 may be configured to provide the required functionality, for example by loading to memory and activating the software modules stored on storage device 512 detailed below.

Computing platform 500 may comprise a communication device 508 for communicating with other devices or other computing platforms, for example obtaining information from the catheterization controller, storing data on remote storage devices, or the like. Communication module 508 may be adapted to interface with any communication channel such as Local Area Network (LAN), Wide Area Network (WAN), cellular network or the like, and use any relevant communication protocol.

Computing platform 500 may comprise a storage device 512, such as a hard disk drive, a Flash disk, a Random Access Memory (RAM), a memory chip, or the like. In some exemplary embodiments, storage device 512 may retain program code operative to cause processor 504 to perform acts associated with any of the modules listed below, or steps of the method of FIG. 4 above. The program code may comprise one or more executable units, such as functions, libraries, standalone programs or the like, adapted to execute instructions as detailed below.

Alternatively or additionally, the provided instructions may be stored on non-transitory tangible computer-readable media, such as magnetic, optical, or electronic memory.

Storage device 512 may comprise I/O module 516, for rendering a display to the user to be displayed over display device 27, such as a map of the heart, a plot of an electrical signal, or the like. I/O module 516 may also be operative in receiving instructions and operation parameters from controls operated by the user, or the like.

Storage device 512 may comprise communication module 520 for transmitting and receiving data to and from other systems, such as the catheter control system, external storage devices, or the like.

Storage device 512 may comprise statistical analysis module 524, which may comprise or implement one or more methods for statistical analysis of signals, such as signals received from an electrode.

In some embodiments, statistical analysis module 524, may comprise or implement autocorrelation calculation module 526 for determining the autocorrelation coefficients for a given signal, as detailed in association with FIGS. 3A and 3B above.

Storage device 512 may comprise statistical analysis comparison module 528, which may comprise or implement one or more methods for comparing the results of applying the statistical analysis to two signals, thereby determining a similarity measure between the two signals.

In some embodiments, statistical analysis comparison module 528 may comprise or implement autocorrelation comparison module 530 for comparing two series of auto-correlation coefficients, obtained by performing autocorrelation over two signals, such as a first signal obtained when the electrode is located away from the heart wall and a second signal obtained when the electrode is positioned on the heart wall.

Storage device 512 may comprise arrhythmogenic region determination module 532, for determining whether a particular comparison result between the two signals is indicative of an arrhythmogenic region where the electrode touched the heart wall. Determination may be performed, for example, by counting the number of corresponding coefficients of the two signals that differ in at most a predetermined value, a predetermined ratio, or the like. If the number of such close coefficient pairs exceeds a second predetermined threshold, the signals may be assumed to be similar, and the region may be assumed to be non-arrhythmogenic.

Storage device 512 may comprise data and control flow management module 536, for activating the modules above in the correct order and with the required input, for example activating statistical analysis comparison module 528 once the statistical analysis results are available for two signals.

It is appreciated that the steps and modules disclosed above are in addition to the software, hardware, firmware or other modules required for operating the catheter, displaying the catheterization process, performing other calculations such as complex fractionated electrogram (CFE) analysis, generating the heart map, or the like. Further details for methods and systems may be found, for example in U.S. Pat. Nos. 8,676,305, 9,629,567, incorporated herein by reference in their entirety for any purpose.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture instructions, machine instructions, machine dependent instructions, microcode, firmware instructions, state-setting data, or either source code or object code written in any combination of one or more programming languages, programming languages such as Java, C, C++, Python, or others. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

EXAMPLES

Example 1

A method comprising: (a) obtaining a first electrical signal from a catheter comprising a first electrode distally disposed thereon, when the catheter is inserted into a chamber of a heart and the first electrode does not touch a wall of the chamber; (b) performing statistical analysis of the first electrical signal to obtain at least one first characteristic of the first electrical signal; (c) obtaining a second electrical signal from the catheter, when a second electrode touches a point on the wall of the chamber; (d) performing statistical analysis of the second electrical signal to obtain at least one second characteristic of the second electrical signal; (e) determining a similarity measure between the at least one first characteristic and the at least one second characteristic; and (f) subject to the similarity being below a predetermined threshold, indicating the region as potentially belonging to an arrhythmogenic region of the heart.

Example 2

The method according to example 1, wherein the statistical analysis comprises autocorrelation of the first signal and autocorrelation of the second signal, and wherein the at least one first characteristic and the at least one second characteristic comprise autocorrelation coefficients of the first signal and the second signal, respectively.

Example 3

The method according to example 1, further comprising processing the second signal to obtain a characteristic of electrical activity within the arrhythmogenic region.

Example 4

The method according to example 3, further comprising: repeating steps (c)-(f) for a plurality of points on the wall of the chamber; and generating a map representing abnormal electrical activity of the heart or part thereof, based on at least some of the plurality of points having similarity below a threshold between the at least one second characteristic and the at least one first characteristic.

Example 5

The method according to example 4, wherein the plurality of points are points touched by one or more electrodes touching the wall of the chamber.

Example 6

The method according to example 4, further comprising: repeating steps (a)-(f) for a plurality of points in at least two chambers of the heart; and generating a map representing abnormal electrical activity of the heart or part thereof, based on at least some of the plurality of points having similarity below a threshold between the at least one second characteristic and a corresponding at least one first characteristic.

Example 7

The method according to example 1, further comprising indicating the point as a candidate for ablation.

Example 8

The method according to example 1, wherein the first electrical signal is an aggregation of a plurality of first signals, wherein the first signals are obtained from a plurality of electrodes distally disposed on the catheter, and wherein the first signals are obtained when at least some of the plurality of electrodes do not touch a wall of the chamber.

Example 9

The method according to example 8, wherein the aggregation is an average or an average with removed.

Example 10

The method according to example 8, wherein the first electrical signal is based only on first signals obtained from electrodes that do not touch the chamber wall.

Example 11

The method according to example 1, wherein the second electrode is the first electrode.

Example 12

The method according to example 1, wherein the similarity measure being above a predetermined threshold is determined by at least a predetermined number of points of the at least one first characteristic each of which is at most at a predetermined difference from corresponding points of the at least one second characteristic.

Example 13

A computerized apparatus having a processor coupled with a memory unit, the processor being adapted to perform the steps of: (a) obtaining a first electrical signal from a catheter comprising a first electrode distally disposed thereon, when the catheter is inserted into a chamber of a heart and the first electrode does not touch a wall of the chamber; (b) performing statistical analysis of the first electrical signal to obtain at least one first characteristic of the first electrical signal; (c) obtaining a second electrical signal from the catheter, when a second electrode touches a point on the wall of the chamber; (d) performing statistical analysis of the second electrical signal to obtain at least one second characteristic of the second electrical signal; €deter- mining a similarity measure between the at least one first characteristic and the at least one second characteristic; and (f) subject to the similarity being below a predetermined threshold, indicating the region as potentially belonging to an arrhythmogenic region of the heart.

Example 14

The apparatus according to example 13, wherein the statistical analysis comprises autocorrelation of the first signal and autocorrelation of the second signal, and wherein the at least one first characteristic and the at least one second characteristic comprise autocorrelation coefficients of the first signal and the second signal, respectively.

Example 15

The apparatus according to example 13, wherein the processor is further adapted to: repeat steps (c)-(f) for a plurality of points on the wall of the chamber; and generate a map representing abnormal electrical activity of the heart or part thereof, based on at least some of the plurality of points having similarity below a threshold between the at least one second characteristic and the at least one first characteristic.

Example 16

The apparatus according to example 13, wherein the first electrical signal is an aggregation of a plurality of first signals, wherein the first signals are obtained from a plural- ity of electrodes distally disposed on the catheter, and wherein the first signals are obtained when at least some of the plurality of electrodes do not touch a wall of the chamber.

Example 17

The apparatus according to example 16, wherein the aggregation is an average or an average with removed outliers.

Example 18

The apparatus according to example 16, wherein the first electrical signal is based only on first signals obtained from electrodes that do not touch the chamber wall.

Example 19

The apparatus according to example 13, wherein the second electrode is the first electrode.

Example 20

A computer program product comprising a non-transitory computer readable medium retaining program instructions, which instructions when read by a processor, cause the processor to perform: (a) obtaining a first electrical signal from a catheter comprising a first electrode distally disposed thereon, when the catheter is inserted into a chamber of a heart and the first electrode does not touch a wall of the chamber; (b) performing statistical analysis of the first electrical signal to obtain at least one first characteristic of the first electrical signal; (c) obtaining a second electrical signal from the catheter, when a second electrode touches a point on the wall of the chamber; (d) performing statistical analysis of the second electrical signal to obtain at least one second characteristic of the second electrical signal; (e) determining a similarity measure between the at least one first characteristic and the at least one second m character- istic; and (f) subject to the similarity being below a prede- termined threshold, indicating the region as potentially belonging to an arrhythmogenic region of the heart.

Although the examples described herein mainly address cardiac diagnostic applications, the methods and systems described herein can also be used in other medical applica- tions.

It will be appreciated that the examples described above are cited by way of example, and that the present disclosure is not limited to what has been particularly shown and described hereinabove. Rather, the scope of the present disclosure includes both combinations and subcombinations of the various features described hereinabove, as well as variations and modifications thereof which would occur to persons skilled in the art upon reading the foregoing descrip- tion and which are not disclosed in the prior art.

The invention claimed is:

1. A method comprising:

sampling output from a catheter while inserted into a heart chamber of a patient, wherein the catheter includes a plurality of electrodes distally disposed thereon and a touch sensor configured for sensing touch of the first electrode with a wall of the heart chamber;

generating an anatomical map of the heart chamber based on the output sampled from the catheter, wherein the output includes a first signal from a first electrode of the plurality a second signal from a second electrode of the plurality and a touch signal from the touch sensor;

identifying that the first electrode is displaced from the wall and the second electrode is touching the wall based pm the touch signal;

identifying an area on the wall at which the second electrode of the plurality captures a signal including a fractionated looking morphology;

verifying that the signal including the fractionated looking morphology originates from arrhythmogenic tissue, wherein the verifying includes:

(a) performing autocorrelation of the first electrical signal to obtain a first series of autocorrelation coefficients;

(b) performing autocorrelation of the second electrical signal to obtain a second series of autocorrelation coefficients, wherein the first signal and the second signal are captured concurrently;

(c) determining a similarity measure between the at least one first series and the second series; and (d) subject to the similarity being below a predeter- mined threshold, verifying that the second signal originates from arrhythmogenic tissue;

rendering the anatomical map on a display; and based on the verifying, annotating the rendering of the anatomical map to indicate location of the arrhythmogenic tissue.

2. The method of claim 1, further comprising processing the second signal to obtain a characteristic of electrical activity within the arrhythmogenic region.

3. The method of claim 2, further comprising:

repeating steps (c)-(f) for a plurality of points on the wall of the chamber; and generating a map representing abnormal electrical activity of the heart or part thereof, based on at least some of the plurality of points having similarity below a threshold between the at least one second characteristic and the at least one first characteristic.

4. The method of claim 3, wherein the plurality of points are points touched by one or more electrodes touching the wall of the chamber.

5. The method of claim 2, further comprising repeating steps (a)-(f) for a plurality of points in at least a second chamber of the heart; and generating a map representing abnormal electrical activity of the heart or part thereof, based on at least some of the plurality of points having similarity below a threshold between the at least one second characteristic and a corresponding at least one first characteristic.

6. The method of claim 1, further comprising indicating the point as a candidate for ablation.

7. The method of claim 1, wherein the first electrical signal is an aggregation of a plurality of first signals, wherein the first signals are obtained from a plurality of electrodes distally disposed on the catheter, and wherein the first signals are obtained when at least some of the plurality of electrodes do not touch the wall of the chamber.

8. The method of claim 7 wherein the aggregation is an average or an average with removed outliers.

9. The method of claim 7 wherein the first electrical signal is based only on first signals obtained from electrodes that do not touch the chamber wall.

10. The method of claim 1, wherein the second electrode is the first electrode.

11. The method of claim 1, wherein the similarity measure being above a predetermined threshold is determined by at least a predetermined number of points of the at least one first characteristic each of which is at most at a predetermined difference from corresponding points of the at least one second characteristic.

12. A catheter-based electrophysiology mapping and ablation system comprising:

a catheter comprising a plurality of electrodes distally disposed thereon and a touch sensor configured for sensing touch of the first electrode with a wall of the heart chamber;

an interface unit configured to sample output from the catheter, wherein the output includes a first signal from a first electrode of the plurality a second signal from a second electrode of the plurality and a touch signal from the touch sensor;

computerized apparatus in communication with the interface unit, wherein the computerized apparatus includes a processor coupled with a memory unit, the processor being adapted to perform the steps of:

generating an anatomical map of the heart chamber based on the output sampled from the catheter, wherein the output includes a first signal from a first electrode of the plurality a second signal from a second electrode of the plurality and a touch signal from the touch sensor;

identifying that the first electrode is displaced from the wall and the second electrode is touching the wall based pm the touch signal;

identifying an area on the wall at which the second electrode of the plurality captures a signal including a fractionated looking morphology;

verifying that the signal including the fractionated looking morphology originates from arrhythmogenic tissue, wherein the verifying includes:

(a) performing autocorrelation of the first electrical signal to obtain a first series of autocorrelation coefficients;

(b) performing autocorrelation of the second electrical signal to obtain a second series of autocorrelation coefficients, wherein the first signal and the second signal are captured concurrently;

(c) determining a similarity measure between the series and the second series; and (d) subject to the similarity being below a predetermined threshold, verifying that the second signal originates from arrhythmogenic tissue;

rendering the anatomical map on a display; and based on the verifying, annotating the rendering of the anatomical map to indicate location of the arrhythmogenic tissue.

13. The apparatus of claim 12, wherein the processor is further adapted to:

repeat steps (c)-(f) for a plurality of points on the wall of the chamber; and generate a map representing abnormal electrical activity of the heart or part thereof, based on at least some of the plurality of points having similarity below a threshold between the at least one second characteristic and the at least one first characteristic.

14. The apparatus of claim 12, wherein the first electrical signal is an aggregation of a plurality of first signals, wherein the first signals are obtained from a plurality of electrodes distally disposed on the catheter, and wherein the first signals are obtained when at least some of the plurality of electrodes do not touch a wall of the chamber.

15. The apparatus of claim 14, wherein the aggregation is an average or an average with removed outliers.

16. The apparatus of claim 14 wherein the first electrical signal is based only on first signals obtained from electrodes that do not touch the chamber wall.

17. The apparatus of claim 12, wherein the second electrode is the first electrode.

* * * * *